United States Patent
Chu (10) Patent No.: US 9,433,486 B2
(45) Date of Patent: Sep. 6, 2016

(54) INCONTINENCE IMPLANT ASSEMBLY

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 178 days.

(21) Appl. No.: 14/195,596

(22) Filed: Mar. 3, 2014

(65) Prior Publication Data

US 2014/0257021 A1  Sep. 11, 2014

Related U.S. Application Data

(60) Provisional application No. 61/775,073, filed on Mar. 8, 2013.

(51) Int. Cl.
| | |
|---|---|
| *A61F 2/00* | (2006.01) |
| *A61B 17/06* | (2006.01) |
| *A61B 17/00* | (2006.01) |

(52) U.S. Cl.
CPC ........ *A61F 2/0045* (2013.01); *A61B 17/06066* (2013.01); *A61B 2017/00805* (2013.01); *A61F 2220/0016* (2013.01); *A61F 2250/006* (2013.01); *A61F 2250/0007* (2013.01)

(58) Field of Classification Search
CPC ........... A61F 2/0045; A61F 2250/006; A61F 2220/0016; A61F 2250/0007; A61B 2017/00805; A61B 17/06066
See application file for complete search history.

(56) References Cited

U.S. PATENT DOCUMENTS

| | | | |
|---|---|---|---|
| 2004/0116944 A1 | 6/2004 | Chu et al. | |
| 2004/0225151 A1 | 11/2004 | Yada et al. | |
| 2004/0225181 A1* | 11/2004 | Chu ................ | A61B 17/06109 600/37 |
| 2005/0256366 A1 | 11/2005 | Chu et al. | |
| 2009/0171142 A1 | 7/2009 | Chu | |
| 2009/0171143 A1* | 7/2009 | Chu ................... | A61B 17/0401 600/37 |

FOREIGN PATENT DOCUMENTS

| | | |
|---|---|---|
| CN | 1484514 A | 3/2004 |
| WO | 2004/016180 A1 | 2/2004 |
| WO | 2014/138103 A2 | 9/2014 |

OTHER PUBLICATIONS

International Search Report and Written Opinion for International Patent Application No. PCT/US2014/020381, mailed Sep. 4, 2014, 13 pages.
International Preliminary Report on Patentability for International Patent Application No. PCT/US2014/020381, mailed Sep. 17, 2015, 9 pages.

* cited by examiner

*Primary Examiner* — Christine H Matthews
*Assistant Examiner* — Joshua D Lannu
(74) *Attorney, Agent, or Firm* — Brake Hughes Bellermann LLP (57) ABSTRACT

An implant assembly for treating incontinence in a patient may include an implant and an elongated member. The implant may include a first arm, a second arm, and a central portion, the first and second arms extending from the central portion. The elongated member may extend along the first arm. The elongated member may include a tail portion at a first end portion of the elongated member, the tail portion having a planar portion, at least part of the tail portion extending beyond the central portion of the implant in a direction opposite from a direction that the first arm extends from the central portion of the implant, an envelope portion, the envelope portion defining a lumen through which the first arm extends, and a window portion comprising a single planar portion extending from the envelope portion.

18 Claims, 9 Drawing Sheets

INCONTINENCE IMPLANT ASSEMBLY

CROSS REFERENCE TO RELATED APPLICATION

This application is a Nonprovisional of, and claims priority to, U.S. Patent Application No. 61/775,073, filed on Mar. 8, 2013, entitled "INCONTINENCE IMPLANT ASSEMBLY", which is incorporated by reference herein in its entirety.

TECHNICAL FIELD

This description relates to slings or implants for incontinence repair.

BACKGROUND

When patients suffer from urinary incontinence, a sling or implant may be placed into the patient's pelvic region to lift the patient's urethra and reduce or eliminate the incontinence. During installation and positioning of the sling or implant, the friction of the sling or implant may cause pain or injury to the patient. To reduce the friction, the sling or implant may be placed into the patient while the sling or implant is inside an elongated member to separate the sling or implant from the patient's tissue. The practitioner may remove the elongated member after placing the sling or implant inside the patient. However, in some cases, the removal of the elongated member may cause the sling or implant to move within the patient, and the sling or implant may become placed too far into the patient's pelvic region or at an incorrect location. For example, friction between the sling or implant and the elongated member may cause the sling or implant to become over tensioned, or over tightened, when the elongated member is removed from the patient's pelvic region.

SUMMARY

According to one general aspect, an implant assembly for treating incontinence in a patient may include an implant and an elongated member. The implant may include a first arm, a second arm, and a central portion, the first and second arms extending from the central portion. The elongated member may extend along the first arm. The elongated member may include a tail portion at a first end portion of the elongated member, the tail portion having a planar portion, at least part of the tail portion extending beyond the central portion of the implant in a direction opposite from a direction that the first arm extends from the central portion of the implant, an envelope portion, the envelope portion defining a lumen through which the first arm extends, and a window portion comprising a single planar portion extending from the envelope portion.

According to another general aspect, an implant may include an implant and first and second strips. The implant may include a central portion and two arms, each of the two arms extending from the central portion. The first strip and second strip may extend on opposite sides of the first arm. The first and second strips may be sealed together on opposing edges. The first strip may extend along less than half of a length of the first arm. The second strip may extend along the entire arm and beyond the central portion of the implant.

According to another general aspect, an implant assembly for treating incontinence in a patient may include an implant and at least a first elongated member. The implant may include a first arm, a second arm, and a central portion, the first and second arms extending from the central portion. A first elongated member may extend along the first arm. The first elongated member may include a tail portion at a first end portion of the elongated member, the tail portion comprising a first open tubular portion, a first envelope portion, the first envelope portion comprising a closed tubular portion extending from the tail portion, the closed tubular portion defining a lumen through which the first arm extends, and a first window portion comprising a second open tubular portion extending from the first envelope portion.

The details of one or more implementations are set forth in the accompanying drawings and the description below. Other features will be apparent from the description and drawings, and from the claims.

DETAILED DESCRIPTION

Figure 1:
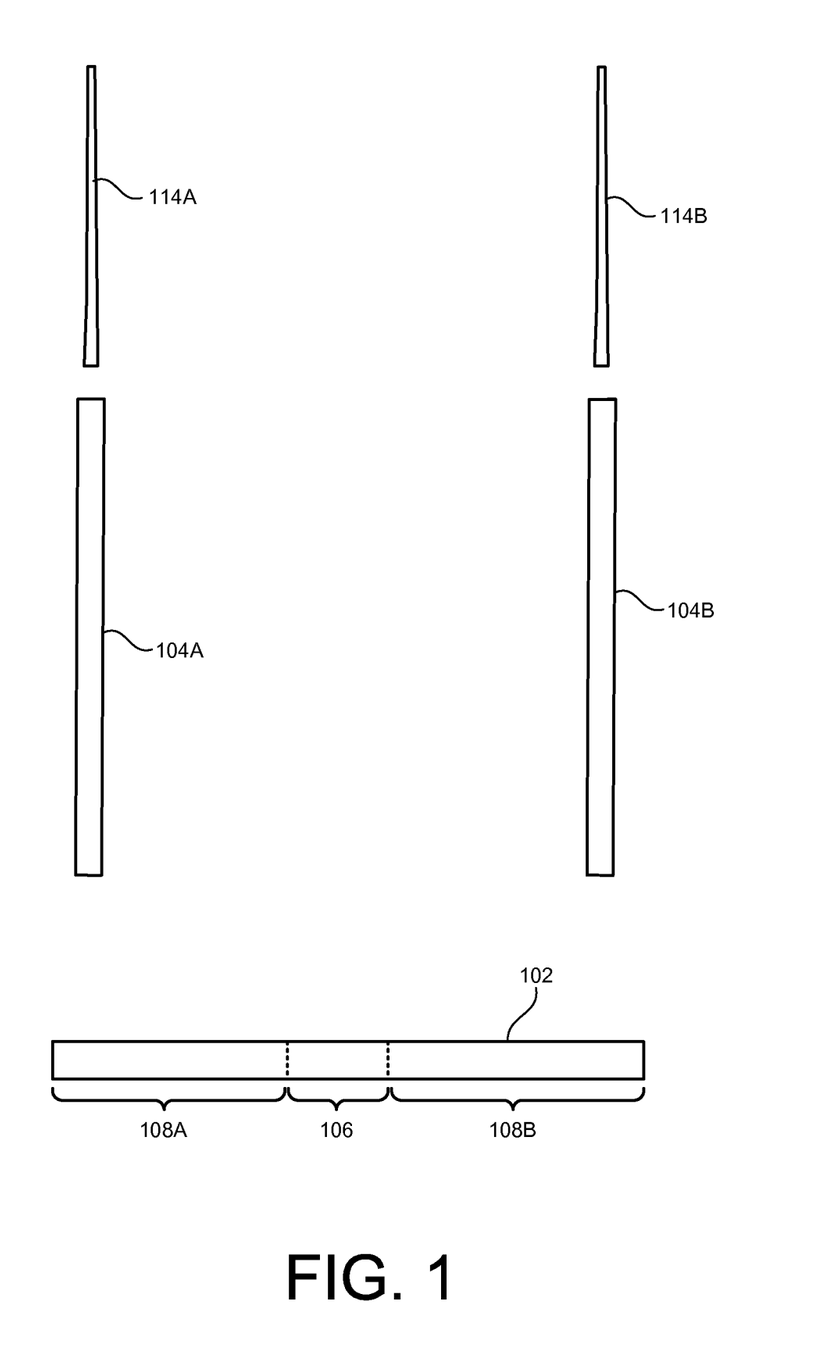
FIG. 1 is a schematic illustration of components of an implant assembly for treating incontinence.

FIG. 1 is a diagram of components of an implant assembly for treating urinary incontinence. The components may be sold individually, collectively, or in any combination of some or all of the components. In an example implementation, the components may be assembled and then sold. The components may be assembled into the forms shown in the below embodiments, and then sold in the assembled forms shown in the below embodiments. The components are not drawn to scale in FIG. 1. A manufacturer may assemble the implant assembly using the parts shown in FIG. 1. After the manufacturer has assembled the implant assembly, the manufacturer may package the implant assembly into a sterile container for delivery to a medical practitioner. The medical practitioner may remove the implant assembly from the sterile container, and use the implant assembly to perform incontinence repair on a patient.

The components may include an implant 102, two elongated members 104A, 104B, and two dilators 114A, 114B, according to an example embodiment. The implant 102 may serve as a sling to hold the patient's urethra in place to relieve incontinence. In some embodiments, the implant 102 is configured to provide support to a portion of a body of a patient. For example, in some embodiments, the implant 102 is configured to be disposed adjacent to and help provide support to a urethra of a patient. The implant 102 may include a flexible mesh, such as polypropylene mesh. The implant 102 may be generally flat, with a width many times, such as five or ten times, a depth or thickness of the implant 102.

The implant or mesh can be made of, or can include, a synthetic material. In some embodiments, the synthetic material can be, or can include, for example, as a polymeric mesh body, a polymeric planar body without mesh cells and structures, and/or so forth. In some embodiments, the synthetic material can include polypropylene, polyester, polyethylene, nylon, polyvinyl chloride (PVC), polystyrene, poly (styrene-isobutylene-styrene (SIBS), and/or so forth. In some embodiments, a mesh body of the synthetic material can be made of a non-woven polymeric material. In some embodiments, the synthetic material can include a Polyform® Synthetic Mesh developed by the Boston Scientific Corporation. The Polyform® Synthetic Mesh can be made from uncoated monofilament macro-porous polypropylene. In some embodiments, the mesh can be formed of or include a woven structure, a non-woven structure, a knitted structure, or a braided structure. In some embodiments, the mesh is tied, twisted, or layered. In some embodiments, the mesh is formed of single or multifilaments. In some embodiments, the mesh is formed of or includes a sheet or a plurality of sheets and may or may not include pores or openings. In some embodiments, the implant 102 or mesh can have a specified weight. In some embodiments, the mesh weight can be approximately between 15 g/cm$^2$ to 35 g/cm$^2$ (e.g., 20 g/cm$^2$, 25 g/cm$^2$, 30 g/cm$^2$). In some embodiments, the mesh can be made, at least in part, of a synthetic material because the synthetic material can have a relatively high strength that can support a bodily portion (e.g., a urethra of a patient) without deforming (e.g., sagging, stretching) over time in an undesirable fashion compared with other materials.

The implant 102 may be divided into a central portion 106 and arms 108A, 108B. The central portion 106 may extend from a center of the implant 102. The arms 108A, 108B may extend from the central portion 106 to end portions of the implant 102. When the implant assembly is assembled, the arms 108A, 108B may partially or fully extend in and/or through a lumen(s) or tunnel(s) of one or both of the elongated members 104A, 104B. The arms 108A, 108B may extend through and/or along the elongated members 104A, 104B and/or dilators 114A, 114B. The central portion 106 may be loose, and not extend along or through the elongated members 104A, 104B or dilators 114A, 114B.

The elongated members 104A, 104B may facilitate the installation of the implant 102 into the patient. The assembler of the implant assembly may insert part or all of one or both arms 108A, 108B of the implant 102 along or through one or both of the elongated members 104A, 104B. The elongated members 104A, 104B may, for example, include envelope portions or tubes defining lumens or tunnels through which the arms 108A, 108B of the implant 102 may be inserted. The envelope portions or tubes defining lumens or tunnels of the elongated members 104A, 104B may separate the arms 108A, 108B from the tissues of the patient, reducing friction while the implant 102 is installed into the patient.

The lumens or tunnels may not be continuous through the elongated members 104A, 104B. The elongated members 104A, 104B may, for example, include open or window portions, along which or though which the arms 108A, 108B may extend. Along the window portions, one side of the arms 108A, 108B may be protected or separated from the patient's tissues, whereas an opposite side of the arms 108A, 108B may be exposed to the patient's tissues. The window portions of the elongated members 104A, 104B may reduce friction between the arms 108A, 108B and the elongated members 104A, 104B. The reduced friction may allow the practitioner to remove the elongated members 104A, 104B from the patient, after placing the implant 102 into a desired location within the patient, without also moving the implant 102 from the desired location.

The implant assembly may also include dilators 114A, 114B. The dilators may each extend from, and/or be attached to, one of the elongated members 104A, 104B. The dilators 114A, 114B may be attached to the tip or end of the respective elongated member 104A, 104B. The dilator 114A, 114B may be attached to the tip or end of the elongated member 104A, 104B by, for example, heat bonding. One of the arms 108A, 108B may extend along each of the dilators 114A, 114B. Connectors (not shown in FIG. 1) may be attached to ends of the dilators 114A, 114B opposite from the elongated members 104A, 104B to which the dilators 114A, 114B are respectively attached. For example, in some embodiments, the connectors are loops, such as suture loops or loops of material. The loops may lead the implant 102 as the practitioner inserts the implant 102 into the patient.

In some embodiments, the dilators 114A, 114B may have a large length. For example, in some embodiments, the dilators 114A, 114B may be longer than the length of the implant 102. In other embodiments, the dilators 114A, 114B may have a small length. For example, in some embodiments, the dilators 114A, 114B may be shorter than the length of the implant 102. The dilators 114A, 114B may be of any cross-sectional shape. For example, the dilators 114A, 114B may have a round or circle cross-sectional shape or may have a different cross-sectional shape, such as a rectangular, square, or oval cross-sectional shape.

Figure 9:
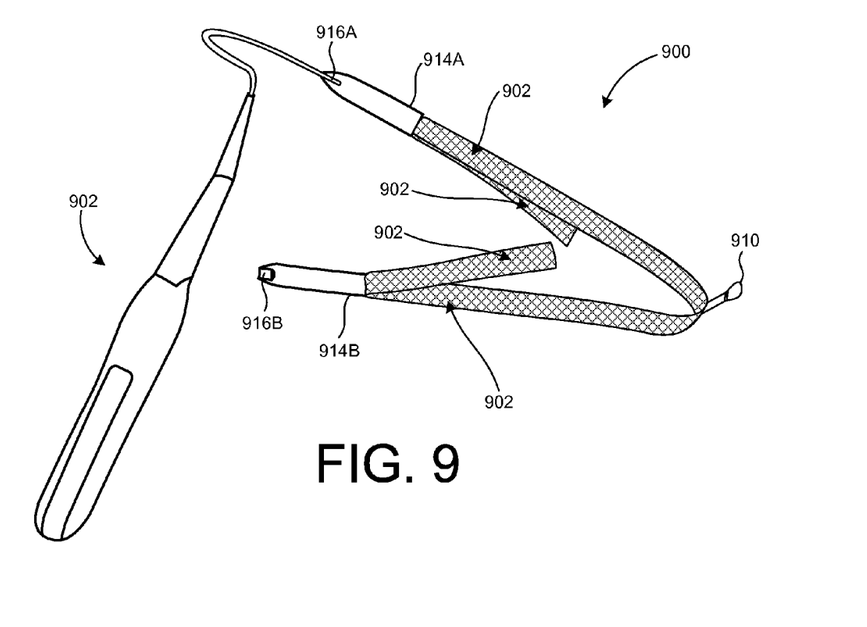
FIG. 9 illustrates an implant assembly for implanting an incontinence implant, and the implant attached thereto, and a delivery device, according to an example embodiment.

With the arms 108A, 108B of the implant 102 extending through the lumens or tunnels of the respective elongated members 104A, 104B and attached to the loops of the respective dilators 114A, 114B, the practitioner may install the implant assembly into the patient. The practitioner may, for example, insert the implant assembly into the patient's pelvic region through a vaginal incision. The practitioner may attach a delivery device (such as a delivery device as shown in FIG. 9) to the loops of the dilators 114A, 114B, and use the delivery device to drive or pull the implant assembly into the patient's pelvic region, or may insert needles through the dilators 114A, 114B and use the needles to drive, push, or pull the implant assembly into the patient's pelvic region, according to example embodiments.

The practitioner may place the implant assembly into the patient so that the central portion 106 of the implant 102 surrounds, or is disposed adjacent to, and supports the patient's urethra (or other portion of the body of the patient). In other embodiments, the implant assembly may be placed in other locations within the body of a patient and used to support other tissue or portions of the body of the patient.

During the implantation process, the dilators 114A, 114B may extend out of incisions or openings in the patient's pelvic region. The practitioner may pull the dilators 114A, 114B forward to tension the implant 102 around the patient's urethra. After tensioning the implant around the patient's urethra, the practitioner may remove the dilators 114A, 114B from the elongated members 104A, 104B. The practitioner may then remove the elongated members 104A, 104B from the implant 102. To remove the elongated members 104A, 104B from the implant 102, he practitioner may cut the implant 102 or mesh at the window of the respective elongated member to release the elongated members 104A, 104B, for example, and thereafter remove the elongated members 104A, 104B from the implant 102 and the patient's pelvic region.

The implant 102 may include tangs at ends of or along the edges of the arms 108A, 108B. The tangs may include cut fibers or jagged edges. In some embodiments, the tangs are configured engage the bodily tissue of the patient to help retain or hold the implant in place within the body of the patient. In other embodiments, the implant may not include tangs. In such embodiments, the implant may be detanged by heating or otherwise removing the tangs.

In another example, the practitioner may cut both the elongated members 104A, 104B and the arms 108A, 108B of the implant 102. The practitioner may, for example, cut both the respective elongated member 104A, 104B and arm 108A, 108B at a window portion 226, 326, 426, 526, 626 (described below). After cutting both the respective elongated member 104A, 104B and arm 108A, 108B, the practitioner may remove the elongated members 104A, 104B from the implant and from the body of the patient.

In some embodiments, the implant assembly includes a tab (shown in FIGS. 2A, 2B, 4, 7, 8, 9, 10, and 11), and the practitioner may also remove the tab from the implant 102 after installing the implant 102 within the body of the patient. The arms 108A, 108B of the implant 102 may hold the implant 102 in place within the patient. The patient's tissues may heal around the implant 102, securing the implant 102 within the patient's pelvic region and supporting the patient's urethra, reducing or ending incontinence. Features of the components described with respect to FIG. 1 may also apply to any or all of the components shown in, and described with respect to, subsequent figures.

In some embodiments, the implant assembly includes a coating or coating materials. For example, in some embodiments, the implant 102 includes a lubricious, hydrophobic, or hydrophilic coating. In other embodiments, another portion or component of the implant assembly, such as the elongate members or the dilators, includes a lubricious, hydrophobic, or hydrophilic coating.

Figure 2A:
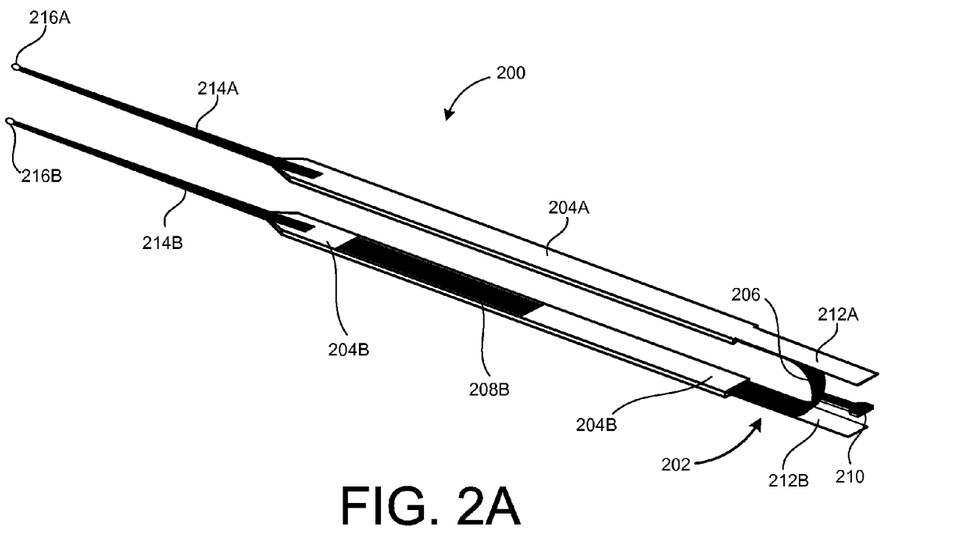
FIGS. 2A and 2B illustrate an implant assembly for implanting an incontinence implant, including an implant and two elongated members, according to an example embodiment.
Figure 2B:
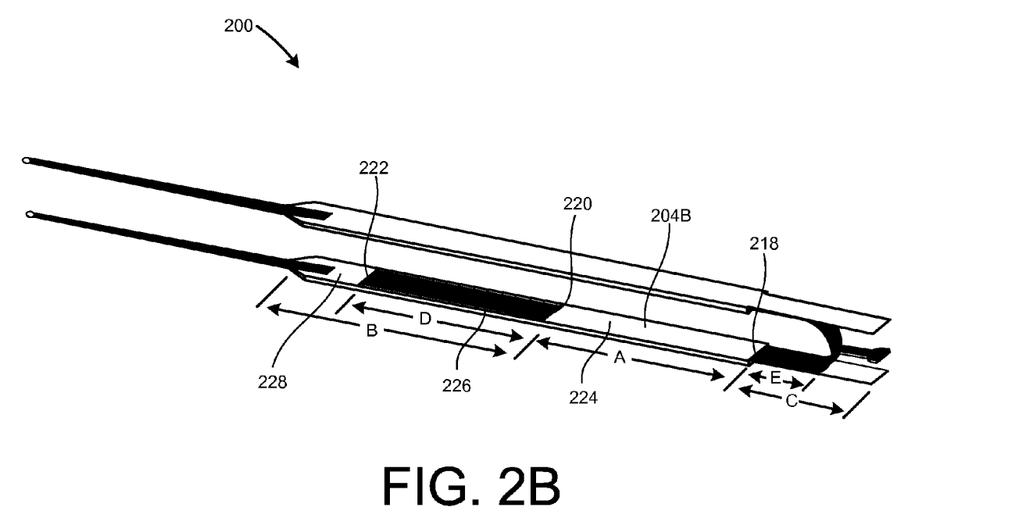

FIGS. 2A and 2B illustrate an implant assembly 200 for implanting an incontinence implant, including an implant 202 and two elongated members 204A, 204B, according to an example embodiment. FIGS. 2A and 2B show the same implant assembly 200, with two figures being used for ease of reference to the descriptors.

The implant 202, which is shown with dark shading in FIGS. 2A, 2B, 3, 4, 10, and 11, is elongated, flexible, and may be planar when laid flat on a surface such as a table. A length of the implant 202 may be many times, such as at least ten times, a width of the implant 202. The width of the implant 202 may also be many times, such as at least five times, a depth or thickness of the implant 202. While the example implant 202 shown in FIGS. 2A and 2B is in a U-shaped position, the implant 202 may also be in a V-shaped, curved, or a more straight position once placed within the body of the patient. A practitioner may place the implant 202 into the patient with the desired shape, and the shape of the implant 202 (which may be flexible) may change while the implant 202 is inserted, tensioned, and/or de-tensioned inside the patient. In some embodiments, the implant if formed of a mesh material.

The implant assembly 200 may include one or two elongated members 204A, 204B extending along the implant 202. The elongated members 204A, 204B are shown in light colors, without shading, in the figures. The elongated members 204A, 204B may be partially tubular, or have two planar layers with one layer shorter than the other, so that the elongated members 204A, 204B fully cover one side of a portion of the implant 202 but only partially cover the opposite side of the same portion of the implant 202.

The implant 202 may be divided into a central portion 206, in the middle of the implant 202, a first arm (not shown in FIGS. 2A and 2B because it is covered by a first elongated member 204A) extending from the central portion 206, and a second arm 208B extending from the central portion 206. The first and second arms 208A, 208B, referred to non-specifically as arms 208, may extend through the portions of the first and second elongated members 204A, 204B which are tubular (or define lumens) and may also include second planar portions. When the practitioner is inserting the implant assembly 200 into the patient, the practitioner may position the implant assembly 200 so that the arms 208 are parallel to each other, and the elongated members 204A, 204B, when receiving the arms 208, may also be positioned parallel to each other. However, the flexibility of the central portion 206, as well as the arms 208A, 208B, may allow the practitioner to position the arms 208A, 208B and elongated members 204A, 204B in various locations and directions relative to each other.

The implant assembly 200 may also include dilators 214A, 214B. The dilators 214A, 214B may extend from the elongated members 204A, 204B. The dilators 214A, 214B may be thin and narrower than the elongated members 204A, 204B from which the dilators 214A, 214B extend. The dilators 214A, 214B may be sufficiently thin and narrow to penetrate tissues of the patient and thereby enable insertion of the implant assembly 200 into the patient.

The dilators 214A, 214B may include loops 216A, 216B. The loops 216A, 216B may be circular or oval-shaped. The loops 216A, 216B may be used associate the implant assembly 202 to a delivery device, such as a needle. The insertion device may then be used to hold and guide the implant assembly 202 into the body of the patient. For example, the practitioner may insert a portion of a delivery device (shown in FIG. 9) into the loops 216A, 216B to drive and/or guide insertion of the implant assembly 200 into the patient. In other embodiments, the dilators include a coupling member (other than a loop) that is configured to associate the implant assembly with a delivery device.

In an example implementation, the implant assembly 200 may include a tab 210 extending from the central portion 206 of the implant 202. The tab 210 may be planar, having a length and width substantially, such as at least five times, greater than a depth or thickness of the tab 210. The tab 210 may extend at an angle with respect to the plane of the implant 202. For example, in some embodiments, the tab 210 may extend perpendicularly from the portion of the central portion 206 of the implant 202 to which the tab 210 is attached (or perpendicularly from the plane in which the portion of the central portion 206 of the implant 202 is disposed). If the implant 202 is positioned in a U-shape or V-shape, the tab 210 may extend from the central portion 206 in a generally opposite direction from the direction that the arms 208 extend from the central portion 206. The tab 210 may, for example, be stitched, sewn, tied, glued, or welded onto the central portion 206 of the implant 202, according to example embodiments.

A practitioner may hold the tab 210 and use the tab 210 to guide insertion of the implant assembly 200 into the patient. The tab 210 may indicate a center length or direction of the implant 202. The practitioner may also use the tab 210 to reduce the tension or adjust placement of the implant 202 on the patient's urethra, by pulling back on the tab 210 to pull the implant 202, as well as other parts of the implant assembly 200, out of the patient's pelvic region and toward the vaginal incision. The practitioner may also pull back on the tab 210 to reposition the implant 202 and other parts of the implant assembly 200 within the patient's pelvic region.

The practitioner may hold and use tail portions 212A, 212B of the elongated members 204A, 204B to guide insertion of the implant assembly 200 into the patient's pelvic region. The elongated members 204A, 204B may each include a tail portion 212A, 212B which extends beyond the central portion 206 of the implant 202 when the implant 202 is inserted into the elongated members 204A, 204B. The tail portions 212A, 212B may be considered the portions of the elongated members 204A, 204B along which no portion of the implant 202 extends, may be considered the portions of the elongated members 204A, 204B on end portions of the elongated members 204A, 204B opposite from the dilators 214A, 214B, or may be considered portions of the elongated members 204A, 204B that end at a first opening 218 of the elongated member 204A, 204B where first envelope portions 224 (discussed below) begin.

The tail portions 212A, 212B maybe be of any shape or size. For example, in some embodiments, the tail portions 212A, 212B are rectangular. In other embodiments, they are of another shape. For example, the tail portions 212A, 212B may have a rounded shape. In some embodiments, the tail portions 212A, 212B are larger or wider than other portions of the elongated members 204A, 204B.

FIG. 2B shows lengths of portions of the second elongated member 204B. Portions of the first elongated member 204A may have similar lengths to the shown lengths of the second elongated member 204B. The tail portion 212B may have only a single planar portion or an open tubular portion. In the example in which the tail portion 212B is considered the portion of the second elongated member 204B that ends at the opening 218 where the first envelope portion 224 begins, the tail portion 212B may have a length of C as shown in FIG. 2B. A portion of the tail portion 212B, having a length E as shown in FIG. 2B, may extend along one side of the second arm 208B, leaving the opposite side exposed. A remaining portion of the tail portion 212B, having a length ((length C minus length E), may extend beyond the central portion 206, and not be in contact with the arm 208 or any other portion of the implant 202. In an example in which the tail portion 212B is the portion of the second elongated member 204B along which the implant 202 does not extend, the tail portion 212B may have the length (length C minus length E).

The practitioner may hold and apply pressure to the tail portions 212A, 212B to guide the implant assembly 200 within the patient. The tail portions 212A, 212B may extend from a midline incision or vaginal incision. A practitioner can control the tail portions 212A, 212B to individually adjust each elongated member 204A, 204B and its corresponding arm 208A, 208B of the implant assembly 200. The practitioner may pull or twist the tail portions 212A, 212B separately, adjusting one arm 208A, 208B of the implant 202 at a time. The practitioner may thereby precisely place each arm 208A, 208B and elongated member 204A, 204B individually. The practitioner may also align the two tail portions 212A, 212B together to approximate a center of the implant 202. The two tail portions 212A, 212B may be clamped together during insertion of the implant assembly 200. The practitioner may clamp the two tail portions 212A, 212B together using, for example, a medical clamp.

The length of the tail portions 212A, 212B, can be lengthened or shortened to lengthen or shorten an exposed portion of the sling. The tail portions 212A, 212B may be lengthened or shortened by trimming the tail portions 212A, 212B. The practitioner may, for example, trim the tail portions 212A, 212B before inserting the implant assembly 200 into the patient. Alternatively, the manufacturer may trim or shape the tail portions 212A, 212B to a desired length. The exposed length of the implant 202 (length C minus length E, where the E is not considered exposed because this portion of the implant 202 is resting against E) may be the length by which the end portions 212A, 212B extend beyond the center portion 206 of the implant 202. The length of E may be zero, so that all of the tail portion 212A, 212B extends beyond the center portion 206. The length A, which may be considered a length of a first envelope portion 224, may be equal to or less than one-fourth of either the length of the implant 202 or the length of the implant assembly 200, or equal to or less than one-half of either the length of the implant 202 or the length of the implant assembly 200. The exposed portion of the implant 202 extending beyond the first envelope portion 224, which may have a length of twice E, may allow the implant 202 to contour and stretch under the urethra, allowing the practitioner to precisely place the implant 202.

The total length of the implant assembly 200, from the loops 216A, 216B of the dilators 214A, 214B to the central portion 206 of the implant 202, end of the tab 210, and/or end of the tail portions 212A, 212B, may be long enough for the implant assembly 200 to exit the skin on both sides of the patient, i.e., the dilators 216A, 216B and portions of the elongated members 204A, 204B may exit the pelvic region of the patient through holes or incisions, and the tail portions 212A, 212B may exit the vaginal incision into the vagina. In an example implementation, at least a portion of the implant assembly 200 of length D, and in some implementations also a portion of the implant assembly 200 of length A, extends from the skin of the patient out of the pelvic region before the practitioner removes the dilators 214A, 214B, elongated members 204A, 204B, and tab 210 from the patient's body and cuts the implant 202 at the skin level of the patient. The entire length of the implant 202 inserted with use of the implant assembly 200 may, for example, be between five and fifty centimeters, such as forty-two centimeters long.

Once the implant assembly 200 has been inserted into the patient, the implant 202 may be removed from the elongated members 204A, 204B. With the dilators 214A, 214B and portions of the elongated members 204A, 204B extending out of the patient's pelvic region, the practitioner may remove the dilators 214A, 214B from the elongated members 204A, 204B. The practitioner may then cut the elongated members 204A, 204B along the section denoted by length D and pull the elongated members 204A, 204B out of the patient's body, leaving the implant 202 in the patient's body. The practitioner may then cut the implant 202 off at the skin level of the patient, so that the implant 202 does not extend outside the patient. The patient's tissues may heal around the implant 202, securing the implant 202 within the patient. The practitioner may also remove the tab 210 by cutting, breaking, or detaching an end of the tab 210 from the implant 202.

The elongated members 204A, 204B may also include first envelope portions 224 (not visible on the first elongated member 204A in FIGS. 2A and 2B) of length A, which may be about ten centimeters. The first envelope portions 224 may be tubular, or may include two planar portions connected at opposite edges. The first envelope portions 224 of the elongated members 204A, 204B may fully surround the portion of the arms 208 extending through the first envelope portions 224.

The elongated members 204A, 204B may also include first window portions 226 extending from the first envelope portions 224. The first window portions 226 may have a length of D as shown in FIG. 2B. The first window portions 226 may include a single planar portion or an open tubular portion, extending along one side of the arm 208 but leaving the opposite side of the arm 208B exposed. The first window portions 226 may reduce the friction between the arms 108A, 108B and elongated members 204A, 204B compared to the friction within the envelope portions 224, facilitating removal of the elongated members 204A, 204B after the implant assembly 200 has been positioned within the patient, without pulling the implant 202 with the elongated members 204A, 204B.

The elongated members 204A, 204B may also include a second envelope portion 228 having a length of (length B minus length D). The second envelope portions 228 may have two planar portions connected at opposite edges, or may be tubular, defining lumens or tunnels, so that the second envelope portions 228 fully surround the portion of the arm 208 extending through the second envelope portion 228.

The elongated members 204A, 204B may include openings or apertures 218, 220, 222 at intersections between the tail portion 212B and the first envelope portion 224, between the first envelope portion 224 and the first end portion 226, and between the first end portion 226 and the second envelope portion 228. After the implant assembly 200 has been inserted into the patient, the practitioner may cut the elongated members 204A, 204B and pull the implant assembly 200 out of the patient, allowing the implant 202 to slide out of the envelope portions 224, 228 through the openings or apertures 218, 220, 222, off of the elongated members 204A, 204B, and remain in place inside the patient. In addition to guiding the implant 202 into the patient, the implant assembly 200 may reduce or eliminate the friction between the implant 202 and the patient's tissues. The envelope portions 224, 228 and window portions 226 of the elongated members 204A, 204B may selectively cover the implant 202 and prevent contact between the implant 202 and the patient, thereby reducing or eliminating the friction between the implant 202 and the patient.

Figure 3:
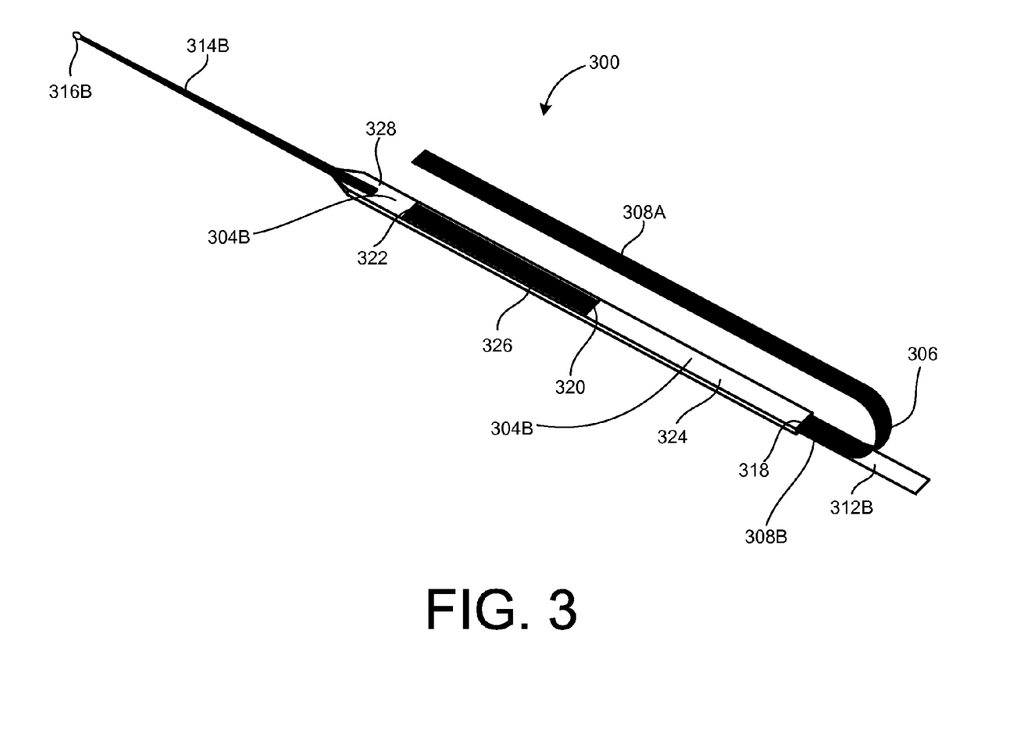
FIG. 3 illustrates an implant assembly for implanting an incontinence sling, including an implant and one elongated member, according to an example embodiment.

FIG. 3 illustrates an implant assembly 300 for implanting an incontinence sling or implant, including an implant 302, one elongated member 308B, and one dilator 314B, according to an example embodiment. Components of the implant assembly 300 may be similar to the components of the implant assemblies shown and described with respect to FIGS. 1, 2A, and 2B. The implant assembly 300 may also include a first elongated member and implant (not shown in FIG. 3)

In the example shown in FIG. 3, the implant assembly 300 includes the second elongated member 304B receiving the second arm 308B of the implant 302 and includes the second dilator 314B, which may be attached to the second elongated member 304B. Also in this example, the implant assembly 300 does not include a tab extending from the central portion 306 of the implant 302. The implant 302 may be threaded into opening 318, through a first envelope portion of the second elongated member 304B, and exit the opening 320. The implant 302 may also be threaded along the window portion 326 into opening 322, threaded through the second envelope portion 328, and secured, such as by heat bonding or tacking, to the second loop 316B.

Figure 4:
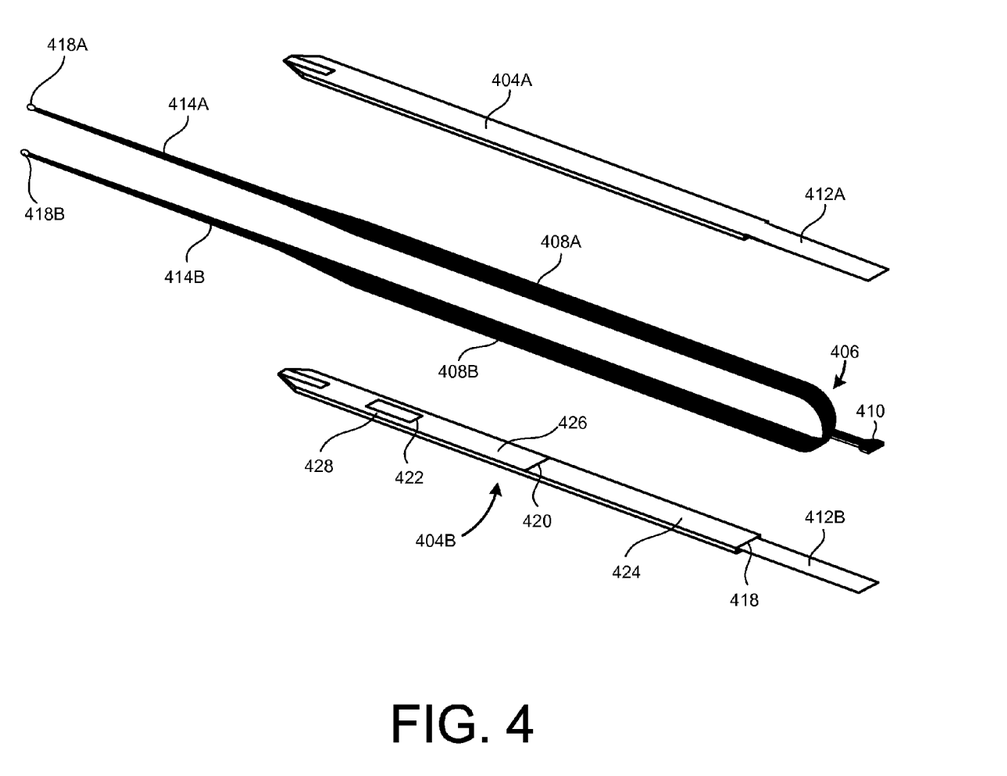
FIG. 4 illustrates the implant and two elongated members, which may be put together to form an implant assembly similar to the implant assembly shown in FIGS. 2A and 2B.

FIG. 4 illustrates an implant 402 and two elongated members 404A, 404B, which may be put together at manufacture to form an implant assembly similar to the implant assembly 200 shown in FIGS. 2A and 2B. The illustration of a first elongated member 404A in FIG. 4 shows that a first side of the elongated members 404A, 404B is continuous and/or flat, and may be formed from a single planar portion or a single continuous side of a tubular member. The illustration of a second elongated member 404B in FIG. 4 shows that a second side of the elongated members 404A, 404B is discontinuous, with a first envelope portion 424 between a first opening 418 and a second opening 420 being raised relative to a tail portion 412B and a first window portion 426, and a second envelope portion 428 beginning at a third opening 422 being raised relative to the first window portion 426. The elongated member 304B shown in FIG. 3 may have similar features to the elongated members 404A, 404B shown in FIG. 4. A tab 410, central portion 406, arms 408A, 408B, dilators 414A, 414B, and loops 418A, 418B may have similar features to the tab 210, central portion 206, arms 208A, 208B, dilators 214A, 214B, and loops 216A, 216B shown and described with respect to FIGS. 2A and 2B.

Figure 5:
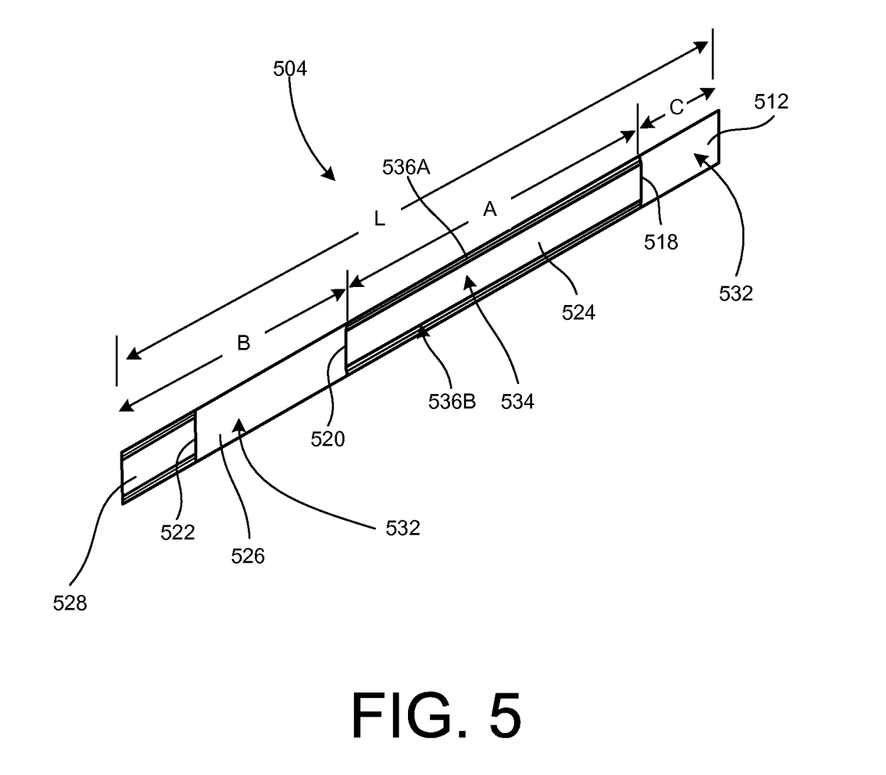
FIG. 5 illustrates an elongated member according to an example embodiment.

FIG. 5 illustrates an elongated member 504 according to an example embodiment. The elongated member 504 may correspond to any of the elongated members 104A, 104B, 204A, 204B, 304B, 404A, 404B shown in FIG. 1, 2A, 2B, 3, or 4. In the example shown in FIG. 5, the elongated member 504 may be manufactured by heat sealing two planar strips 532, 534 together to form the first envelope portion 524, and in some embodiments, a third planar strip to form the second envelope portion 528. The strips 532, 534 may include, for example, polymer. Each polymer strip 532, 534 may include a single material or multiple materials, such as polymer, and may include a single or multiple layers. As discussed above, the first envelope portion 524 may be between the tail portion 512 and the first window portion 526 of the elongated member 504.

The first strip 532 may extend the entire length of the elongated member 504, and may have a length L (or length A plus length B plus length C, wherein the lengths A, B, and C correspond to the lengths shown in FIG. 2B). The second strip 534 may extend only the length A of the first envelope portion 524, forming a second planar portion of the first envelope portion 524 to receive the arm of the implant (shown in FIGS. 2A, 2B, 3, and 4). A first end of the second strip 534 is positioned a distance C from a tail end of the first strip 532, forming the tail portion 512 of length C. If no tail portion 512 is preferred, the ends of the two strips 532, 534 may be aligned, so that the length C is zero. The two planar portions of the first envelope portion 524 may be joined by seals 536A, 536B at opposite edges of the strips 532, 534 or planar portions of the envelope portion 524. The seals 536A, 536B joining the strips 532, 534 or planar portions of the envelope portion 524 may be, for example, heat seals. The sealing of the strips 532, 534 may form a lumen or tunnel of length A, which may be entirely closed except at the ends of the lumen or tunnel, with the ends of the lumen or tunnel being at the openings 518, 520. A second envelope portion

528, which has two layers, of length (length B minus length D) (shown in FIG. 2B) may be formed in a similar manner to the first envelope portion 524.

Figure 6:
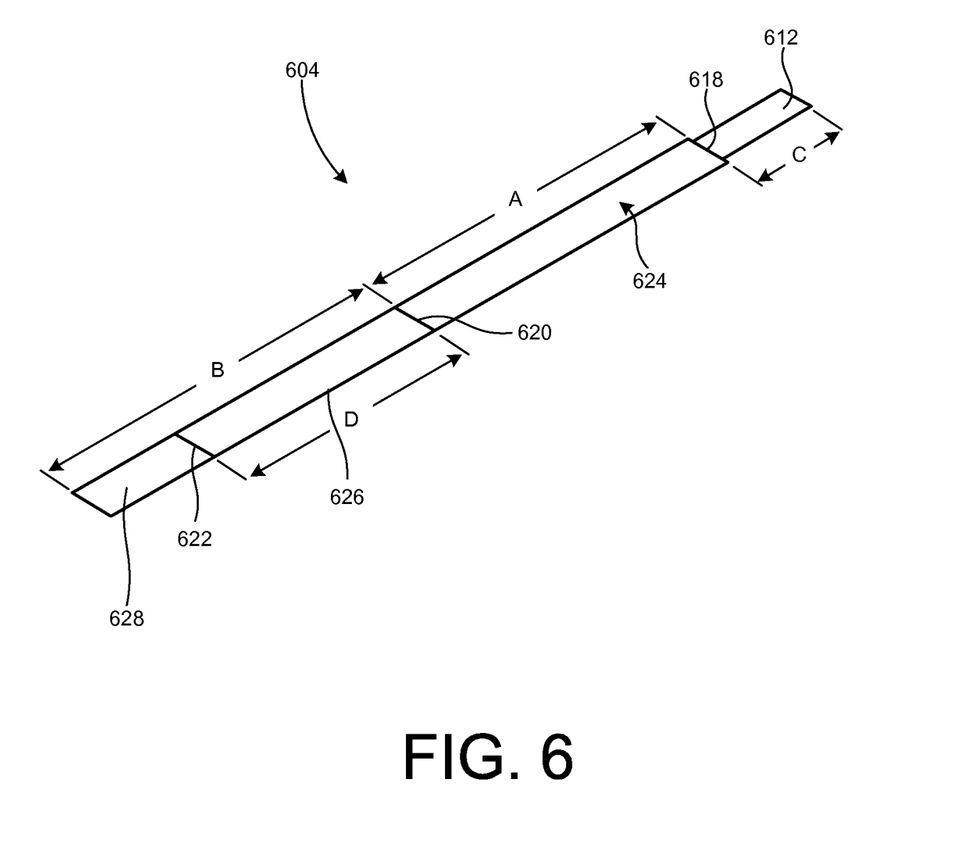
FIG. 6 illustrates an elongated member according to another example embodiment.

FIG. 6 illustrates an elongated member 604 according to another example embodiment. The elongated member 604 may be either the first elongated member or second elongated member shown in FIG. 2A, 2B, 3, or 4. In this example, the elongated member 604 may be made of a tube, such as a thin flat polymer tube. Apertures or slits may be cut into a wall of the tube a length A from each other, forming the openings 618, 620 at opposite ends of the first envelope portion 624. One wall, of length C, of the tube may be removed, such as by cutting, to form the tail portion 612. Another wall, of length D, may also be removed, to form the first window portion 626. The walls may be left intact to form the second envelope portion 628. The apertures or openings 618, 620, 622 may be rectangular, oval, round, square, or polygonal, according to example implementations. The lengths A, B, C, and D shown in FIG. 6 may correspond to the lengths shown in FIG. 2B.

Figure 7:
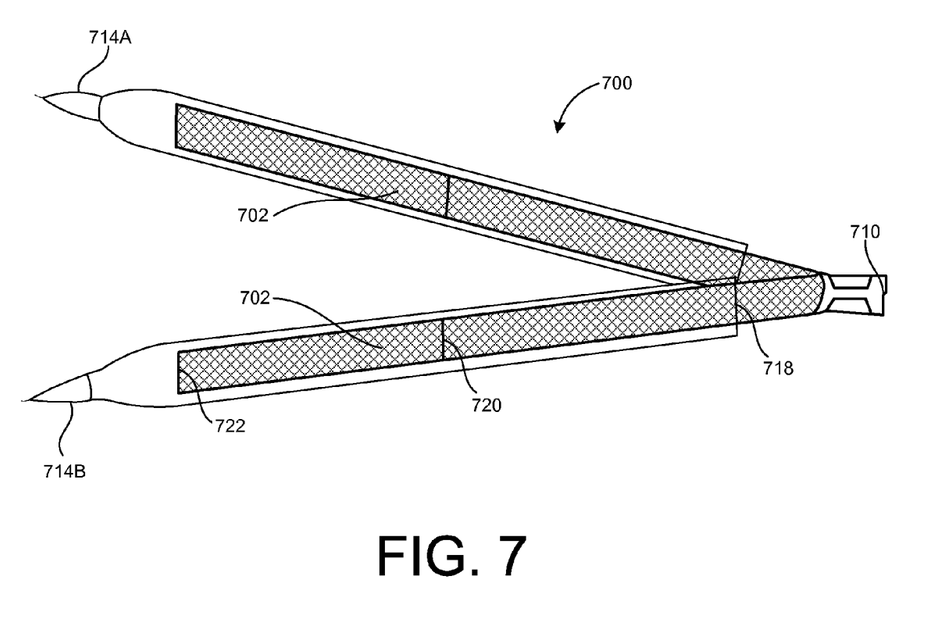
FIG. 7 illustrates an implant assembly for implanting an incontinence implant, and the implant attached thereto, according to an example embodiment.

FIG. 7 illustrates of an implant assembly 700 for implanting an incontinence sling, and the implant 702 attached thereto, according to an example embodiment. The implant assembly 700 may have similar features to the implant assemblies and components described with respect to the preceding figures. The hatching in the implant assembly 700 shows the implant 702. In this example, the dilators 714A, 714B may be shorter than the dilators 114A, 114B, 214A, 214B, 314B discussed in previous examples. The shorter lengths of the dilators 714A, 714B may enable the practitioner to insert the implant assembly 700 into the patient's pelvic region through the vaginal incision without using any other device, because the dilators 714A, 714B may penetrate the patient's tissues independently.

Figure 8:
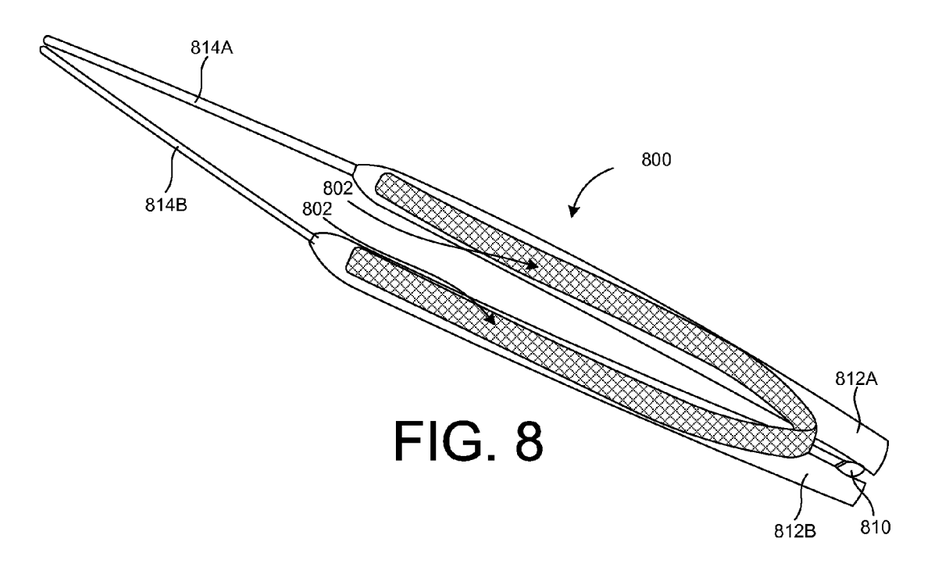
FIG. 8 illustrates an implant assembly for implanting an incontinence implant, and the implant attached thereto, according to another example embodiment.

FIG. 8 illustrates an implant assembly 800 for implanting an incontinence sling, and the implant 802 attached thereto, according to another example embodiment. The implant assembly 800 may have similar features to the implant assemblies and components described with respect to the preceding figures. In the example shown in FIG. 8, the dilators 814A, 814B are hollow, and are configured to receive needles (not shown). The practitioner may place needles through the dilators 814A, 814B. The needles may extend beyond the dilators 814A, 814B. The needles may penetrate the patient's tissues and guide the extension of the dilators 814A, 814B through and out of the patient's pelvic region. After the practitioner has appropriately placed the implant assembly 800 inside the patient, the practitioner may pull the needles out of the dilators 814A, 814B. After pulling the needles out of the dilators 814A, 814B, the practitioner may remove the dilators 814A, 814B, elongated members 804A, 804B, and tab 810, leaving the implant 802 remaining in the patient, as discussed in the previous examples.

FIG. 9 illustrates an implant assembly 900 for inserting an incontinence implant into a patient, and the implant attached thereto, and a delivery device 902, according to an example embodiment. This implant assembly 900 may have similar features to the implant assemblies discussed above. The practitioner may insert the delivery device 902 though a skin incision in the patient such that the delivery device 902 extends from the skin incision and extends out a vaginal incision. In some embodiments, the delivery device 902 may extend through an obturator foramen of the patient. The practitioner may then couple the implant assembly 900 to the delivery device 902. The delivery device 902 may then be pulled or refracted to pull the implant into place within the body of the patient. In the illustrated embodiment, holes or openings 916A and 916B defined by the dilators 914A and 914B may be used to associate or couple the implant assembly 900 to the delivery device 902. A similar procedure may be used to place the opposite arm of the implant assembly into the body of the patient. In the illustrated embodiment, the tab 910, which is coupled to the implant assembly 900 and by be disposed proximate the vaginal incision, may be used to adjust the placement of the implant assembly within the body of the patent. The tab 910 may then be decoupled from the implant and removed from the body of the patient. In some embodiments, the implant assembly includes elongated members that include tail portions. In such embodiments, the tail portions may be used (rather than or in addition to the tab 902) to adjust placement of the implant assembly within the body of the patient.

In the illustrated embodiment, the dilators 914A and 914B define an opening or slot though which the implant 902 may extend. In the illustrated embodiment, the implant 902 extends though the openings or slots and portions of the implant 902 are folded or curved back towards the mid-portion of the implant 902 (for example, where the tab 910 is coupled to the implant 902). The practitioner may adjust the length or amount of the implant that extends through the openings or slots to effectively lengthen or shorten the implant assembly. Accordingly, a practitioner may use adjust the length of the implant assembly based on the size of the patient or the location within the body into which the implant assembly is being placed. In some embodiments, the portion of the implant that is folded and directed towards the mid-portion of the implant may be trimmed prior to insertion of the implant assembly 900 into the body of the patient.

In some embodiments, the implant 902 may be formed of a colored material. In some embodiments, the implant 902 is formed of a blue mesh material and is configured to facilitate the viewing of the implant during the implantation procedure.

In some embodiments, the implant 902 may be coupled to the dilator such as via a heat tack, weld, or an adhesive. In some embodiments, the mid portion of the implant includes tangs and in other embodiments, the mid portion is free of tangs.

Figure 10:
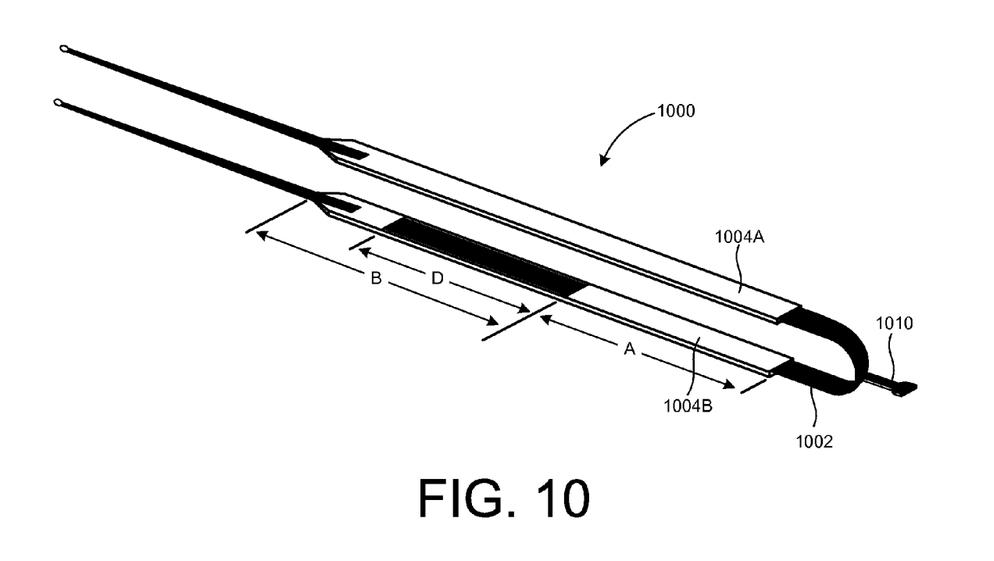
FIG. 10 illustrates an implant assembly for implanting an incontinence implant, including an implant and two elongated members, according to an example embodiment.

FIG. 10 illustrates an implant assembly 1000 for implanting an incontinence implant, including an implant 1002 and two elongated members 1004A, 1004B, according to an example embodiment. In this example, the elongated members 1004A, 1004B do not include tail portions. In other respects, the implant assembly 1000 is similar to the implant assembly 200 shown and described with respect to FIGS. 2A, 2B, and 4. A practitioner may grasp the implant 1002 with forceps, and adjust the implant 1002 inside the patient using the tab 1010.

Figure 11:
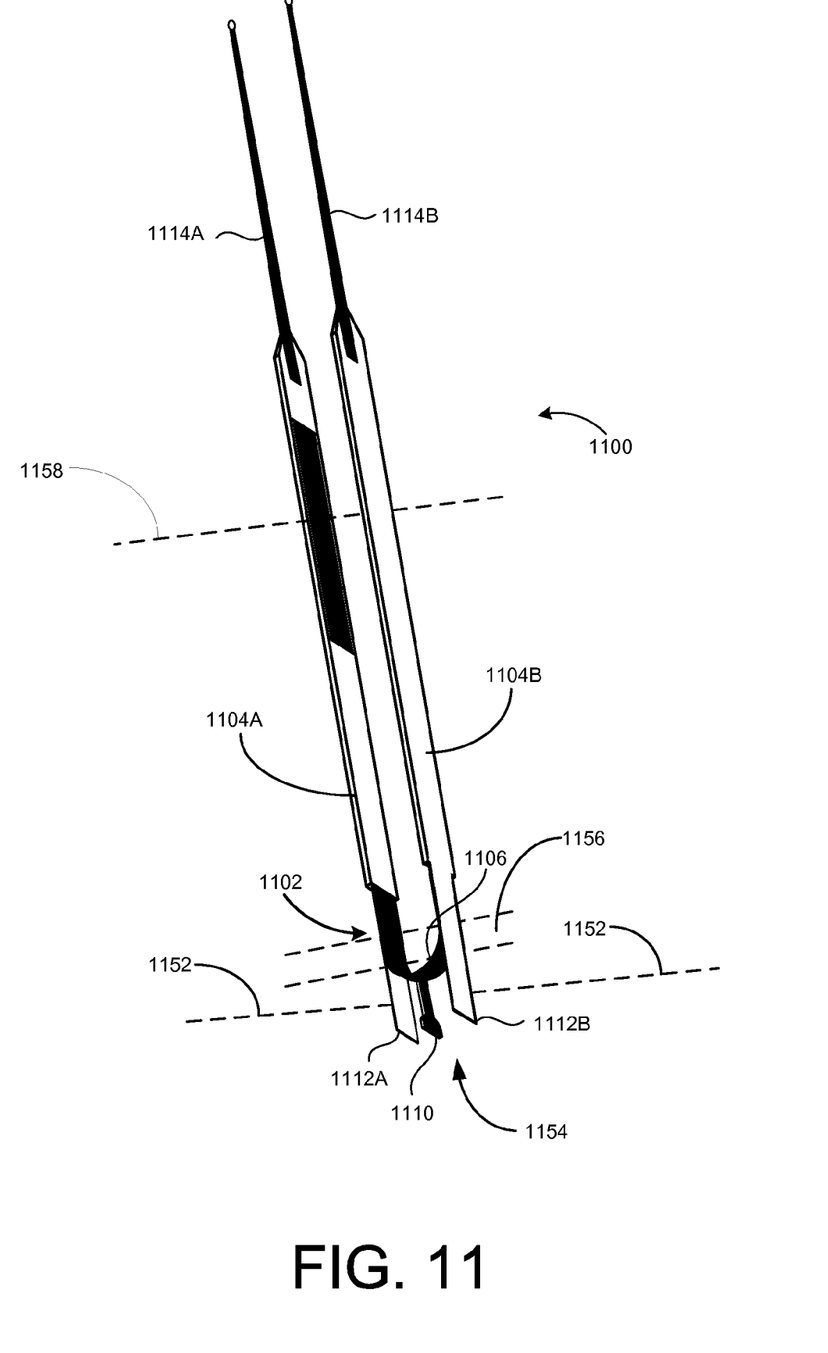
FIG. 11 illustrates an implant assembly inside a body of a patient according to an example embodiment.

FIG. 11 illustrates a diagram of an implant assembly 1100 inside a patient according to an example embodiment. The practitioner may cut a vaginal incision 1154 into a vaginal wall 1152 of the patient's vagina. For example, the practitioner may make an anterior vaginal incision. The practitioner may insert the implant assembly 1100 into the patient's pelvic region by inserting the implant assembly 1100 into the patient's vagina, and driving (by pushing or pulling) the implant assembly 1100 into the patient's pelvic region through the vaginal incision 1154. The implant assembly 1100 may extend out of the patient's pelvic region through the skin incision 1158 of the patient. The central portion 1106 of the implant 1102 may generally surround or extend below the patient's urethra 1156. The practitioner may guide the placement of the implant 1102 around the patient's urethra by moving the tab 1110 and/or tail portions 1112A, 1112B. After the practitioner has placed the implant 1102 in the correct location around the patient's urethra 1156, the practitioner may remove the dilators 1114A, 1114B, elongated members 1104A, 1104B, and tab 1110, and cut the implant 1102 at the level of the patient's pelvic wall 1158. The patient's tissues may heal around the implant 1102, securing the implant 1102 within the patient.

In some embodiments, an implant assembly for treating incontinence in a patient includes an implant having a first arm, a second arm, and a central portion, the first and second arms extending from the central portion; and an elongated member. The elongated member extends along the first arm. The elongate member includes a tail portion at a first end portion of the elongated member. The tail portion has a planar portion, an envelop portion, and a window portion. At least part of the tail portion extends beyond the central portion of the implant in a direction opposite from a direction that the first arm extends from the central portion of the implant. The envelope portion defines a lumen through which the first arm extends. The window portion includes a single planar portion extending from the envelope portion.

In some embodiments, the elongated member includes a polymer material. In some embodiments, the implant includes a mesh material.

In some embodiments, the elongated member is made from a first strip and a second strip. The first strip includes the planar portion of the tail portion, a first planar portion of the envelope portion, and the single planar portion of the window portion. The first strip has a length equal to at least a sum of lengths of the tail portion, the envelope portion, and the first end portion. In some embodiments, the second strip includes a second planar portion of the envelope portion defining the lumen and has a length equal to the length of the envelope portion.

In some embodiments, all of the tail portion (or the tail portion in its entirety) of the elongated member extends beyond the central portion of the implant. In some embodiments, about half of the tail portion extends beyond the central portion of the implant. In some embodiments, the envelope portion is about ten centimeters long. In some embodiments, the elongated member further includes a first aperture at an intersection of the tail portion and the envelope portion; and a second aperture at an intersection of the envelope portion and the window portion.

In some embodiments, the elongated member further includes a second envelope portion and a second window portion. The second envelope portion has a first planar portion extending from the window portion and a second planar portion. The first and second planar portions of the second envelope portion are connected at opposite edges and form a second lumen through which the respective arm extends. The second window portion includes a single planar portion extending from the first planar portion of the second envelope portion.

In some embodiments, the implant assembly includes a dilator. The dilator is narrower than the elongated member and extends from a portion of the elongated member which is opposite from the central portion of the implant.

In some embodiments, the dilator includes a connector at an end portion of the dilator which is opposite from the elongated member from which the dilator extends. In some embodiments, the implant assembly includes a tab extending from the central portion of the implant. The tab extends in a direction which is generally perpendicular to a portion of the central portion from which the tab extends.

In some embodiments, the envelope portion includes first and second planar portions which are heat sealed together at opposite edges. In some embodiments, the implant assembly includes a second elongated member extending along the second arm of the implant.

In some embodiments, an apparatus includes an implant, a first strip, and a second strip. The implant includes a central portion, a first arm, and a second arm. Each of the first and second arms extends from the central portion. The first strip and the second strip extend on opposite sides of the first arm. The first and second strips are sealed together on opposing edges. The first strip extends along less than half of a length of the first arm. The second strip extends along an entirety of the length of the first arm and beyond the central portion of the implant.

In some embodiments, the first and second strips include polymer materials.

In some embodiments, an implant assembly for treating incontinence in a patient includes an implant and at least a first elongated member. The implant includes a first arm, a second arm, and a central portion. The first and second arms extend from the central portion. The first elongated member extends along the first arm. The first elongated member includes a tail portion, a first envelop, and a first window portion. The tail portion is disposed at a first end portion of the elongated member. The tail portion includes a first open tubular portion. The first envelope portion includes a closed tubular portion extending from the tail portion. The closed tubular portion defines a lumen through which the first arm extends. The first window portion includes a second open tubular portion extending from the first envelope portion.

In some embodiments, the first elongated member includes a polymer material. In some embodiments, the implant includes a mesh material. In some embodiments, at least part of the tail portion of the first elongated member extends beyond the central portion of the implant in a direction opposite from a direction that the arms extend from the central portion of the implant.

In some embodiments, the first elongated member includes a thin flat polymer tube. In some embodiments, the first elongated member is made from a tube. The tube has first and second portions cut out to form the tail portion and the first window portion, respectively.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. An implant assembly for treating incontinence in a patient, the implant assembly comprising:
    an implant comprising a first arm, a second arm, and a central portion, the first and second arms extending from the central portion; and
    an elongated member, the elongated member configured to extend along the first arm, the elongated member including:
        a tail portion at a first end portion of the elongated member, the tail portion having a planar portion, at least part of the tail portion extending beyond the central portion of the implant;
        a first envelope portion, the first envelope portion defining a lumen in which the first arm extends through, the tail portion extending from the first envelope portion;

a window portion comprising a single planar portion extending from the first envelope portion; and a second envelope portion at a second end portion of the elongated member, the second envelope portion defining a lumen in which the first arm extends through, the window portion being disposed between the first envelope portion and the second envelope portion.

2. The implant assembly of claim 1, wherein the elongated member includes a polymer material.

3. The implant assembly of claim 1, wherein the implant includes a mesh material.

4. The implant assembly of claim 1, wherein the elongated member includes a first strip, a second strip, and a third strip, wherein:

the first strip comprises the planar portion of the tail portion, a first planar portion of the first envelope portion, the single planar portion of the window portion, and a first planar portion of the second envelope portion, and has a length equal to at least a sum of lengths of the tail portion, the first envelope portion, the window portion, and the second envelope portion;

the second strip comprises a second planar portion of the first envelope portion and has a length equal to the length of the first envelope portion;

the third strip comprising a second planar portion of the second envelope portion and has a length equal to the length of the second envelope portion.

5. The implant assembly of claim 1, wherein all of the tail portion of the elongated member extends beyond the central portion of the implant.

6. The implant assembly of claim 1, wherein about half of the tail portion extends beyond the central portion of the implant.

7. The implant assembly of claim 1, wherein the first envelope portion is about ten centimeters long.

8. The implant assembly of claim 1, wherein the elongated member further includes:

a first aperture at an intersection of the tail portion and the first envelope portion; and a second aperture at an intersection of the first envelope portion and the window portion.

9. The implant assembly of claim 1, wherein the second envelope portion comprising a first planar portion extending from the window portion and a second planar portion, the first and second planar portions of the second envelope portion being connected at opposite edges and forming the lumen of the second envelope portion in which the first arm extends through, wherein the implant assembly further includes a second window portion comprising a single planar portion extending from the first planar portion of the second envelope portion.

10. The implant assembly of claim 9, further including a dilator, the dilator being narrower than the elongated member and extending from a portion of the elongated member which is opposite from the central portion of the implant.

11. The implant assembly of claim 10, wherein the dilator comprises a connector at an end portion of dilator which is opposite from the elongated member from which the dilator extends.

12. The implant assembly of claim 1, further including a tab extending from the central portion of the implant, the tab extending in a direction which is generally perpendicular to a portion of the central portion from which the tab extends.

13. The implant assembly of claim 1, wherein the first envelope portion comprises first and second planar portions which are heat sealed together at opposite edges.

14. The implant assembly of claim 1, further comprising a second elongated member configured to extend along the second arm of the implant.

15. An implant assembly for treating incontinence in a patient, the implant assembly comprising:

an implant comprising a first arm, a second arm, and a central portion, the first and second arms extending from the central portion; and at least a first elongated member, the first elongated member extending along the first arm, the first elongated member comprising:

a tail portion at a first end portion of the elongated member, the tail portion comprising a first open tubular portion;

a first envelope portion, the first envelope portion comprising a closed tubular portion extending from the tail portion, the closed tubular portion defining a lumen in which the first arm extends through;

a first window portion comprising a second open tubular portion extending from the first envelope portion; and a second envelope portion, the second envelope portion defining a lumen in which the first arm extends through, the window portion being disposed between the first envelope portion and the second envelope portion.

16. The implant assembly of claim 15, wherein the first elongated member comprises a polymer material.

17. The implant assembly of claim 15, wherein the implant comprises a mesh material.

18. The implant assembly of claim 15, wherein at least part of the tail portion of the first elongated member extends beyond the central portion of the implant in a direction opposite from a direction that the arms extend from the central portion of the implant.

* * * * *